(12) United States Patent
Sartor et al.

(10) Patent No.: US 10,898,255 B2
(45) Date of Patent: Jan. 26, 2021

(54) BIPOLAR PLASMA CATHETER

(71) Applicant: Covidien LP, Mansfield, MA (US)

(72) Inventors: Joe D. Sartor, Longmont, CO (US); Daniel A. Friedrichs, Aurora, CO (US); William Scott Darrow, Longmont, CO (US)

(73) Assignee: Covidien LP, Mansfield, MA (US)

( * ) Notice: Subject to any disclaimer, the term of this patent is extended or adjusted under 35 U.S.C. 154(b) by 113 days.

(21) Appl. No.: 16/227,285

(22) Filed: Dec. 20, 2018

(65) Prior Publication Data

US 2019/0125425 A1     May 2, 2019

Related U.S. Application Data

(63) Continuation of application No. 15/019,576, filed on Feb. 9, 2016, now Pat. No. 10,159,523.

(51) Int. Cl.
  *A61B 18/04*     (2006.01)
  *A61B 17/00*     (2006.01)
  *A61B 18/14*     (2006.01)

(52) U.S. Cl.
  CPC ...... *A61B 18/042* (2013.01); *A61B 17/00234* (2013.01); *A61B 18/1492* (2013.01); *A61B 2017/00296* (2013.01); *A61B 2017/00526* (2013.01)

(58) Field of Classification Search
  CPC ............ A61B 18/042; A61B 17/00234; A61B 18/1492; A61B 2017/00296; A61B 2017/00526
  USPC .................................................. 604/24, 500
  See application file for complete search history.

(56) References Cited

U.S. PATENT DOCUMENTS

| 3,760,812 | A | 9/1973 | Timm et al. |
| 3,895,635 | A | 7/1975 | Justus et al. |
| 4,413,304 | A | 11/1983 | Gerry |
| 5,693,045 | A | 12/1997 | Eggers |
| 5,831,210 | A | 11/1998 | Nugent |

(Continued)

FOREIGN PATENT DOCUMENTS

| EP | 0061246 A1 | 9/1982 |
| EP | 0750886 A1 | 1/1997 |

(Continued)

OTHER PUBLICATIONS

European Search Report dated Jun. 28, 2017 in corresponding European Patent Application No. 17155111.2, 9 pages.

*Primary Examiner* — Phillip A Gray (74) *Attorney, Agent, or Firm* — Carter, DeLuca & Farrell LLP (57) ABSTRACT

The present disclosure provides a plasma catheter including a tubular member; a conductive cylindrical member; a first electrode; and a second electrode. The tubular member defines a longitudinal lumen therethrough and has a proximal portion and a distal portion. The conductive cylindrical member is disposed at the distal portion of the tubular member. The first electrode is embedded in a first side of the tubular member and coupled to the conductive cylindrical member. The second electrode is embedded in a second side of the tubular member diametrically opposed to the first side. The second electrode is offset from the tubular member and aligned with a center axis defined by the conductive cylindrical member.

13 Claims, 5 Drawing Sheets

(56) References Cited

U.S. PATENT DOCUMENTS

| | | |
|---|---|---|
| 6,113,596 A | 9/2000 | Hooven et al. |
| 6,190,385 B1 | 2/2001 | Tom et al. |
| 6,210,404 B1 | 4/2001 | Shadduck |
| 6,300,573 B1 | 10/2001 | Horie et al. |
| 6,394,949 B1 | 5/2002 | Crowley et al. |
| 7,057,111 B2 | 6/2006 | Fung et al. |
| 7,090,673 B2 | 8/2006 | Dycus et al. |
| 7,147,638 B2 | 12/2006 | Chapman et al. |
| 7,491,200 B2 * | 2/2009 | Underwood ....... A61B 18/1485 128/898 |
| 7,566,333 B2 * | 7/2009 | Van Wyk ........... A61B 18/1485 606/41 |
| 7,819,865 B2 | 10/2010 | Orszulak |
| 8,353,904 B2 | 1/2013 | Orszulak |
| 10,159,523 B2 | 12/2018 | Sartor et al. |
| 2003/0229344 A1 | 12/2003 | Dycus et al. |
| 2004/0088029 A1 | 5/2004 | Yamamoto |
| 2004/0254573 A1 | 12/2004 | Dycus et al. |
| 2005/0049454 A1 | 3/2005 | Ouchi |
| 2006/0148306 A1 | 7/2006 | Desinger et al. |
| 2008/0027504 A1 | 1/2008 | Bedenbaugh |
| 2013/0261536 A1 | 10/2013 | Sartor |
| 2014/0228833 A1 | 8/2014 | Friedrichs et al. |

FOREIGN PATENT DOCUMENTS

| | | |
|---|---|---|
| EP | 1090598 A1 | 4/2001 |
| EP | 2679191 A1 | 1/2014 |
| EP | 2765838 A2 | 8/2014 |
| GB | 2321193 A | 7/1998 |
| GB | 2326519 A | 12/1998 |
| GB | 2521611 A | 7/2015 |
| WO | 9627337 A1 | 9/1996 |
| WO | 2006048199 A1 | 5/2006 |
| WO | 2006081191 A1 | 8/2006 |
| WO | 2008090004 A1 | 7/2008 |

* cited by examiner

BIPOLAR PLASMA CATHETER

CROSS REFERENCE TO RELATED APPLICATION

This application is a continuation application of U.S. patent application Ser. No. 15/019,576, filed on Feb. 9, 2016, the entire contents of which are incorporated by reference herein.

BACKGROUND

Technical Field

The present disclosure relates to plasma devices for surface processing and tissue treatment. More particularly, the disclosure relates to a plasma catheter, a plasma system, and a method of manufacturing a plasma catheter that facilitate efficient delivery of power to a distal treatment portion of the catheter for creating highly energized plasma having sufficient energy to produce a clinical bipolar tissue effect.

Background of Related Art

Electrical discharges in dense media, such as liquids and gases at or near atmospheric pressure, can, under appropriate conditions, result in plasma formation. Plasmas have the unique ability to create large amounts of chemical species, such as ions, radicals, electrons, excited-state (e.g., metastable) species, molecular fragments, photons, and the like. The plasma species may be generated in a variety of internal energy states or external kinetic energy distributions by tailoring plasma electron temperature and electron density. In addition, adjusting spatial, temporal and temperature properties of the plasma creates specific changes to the material being irradiated by the plasma species and associated photon fluxes. Plasmas are also capable of generating photons including energetic ultraviolet photons that have sufficient energy to initiate photochemical and photocatalytic reaction paths in biological and other materials that are irradiated by the plasma photons.

SUMMARY

Plasmas have broad applicability and provide alternative solutions to industrial, scientific and medical needs, especially workpiece (e.g., tissue) surface treatment at any temperature range. Plasmas may be delivered to the workpiece, thereby effecting multiple changes in the properties of materials upon which the plasmas impinge. Plasmas have the unique ability to create large fluxes of radiation (e.g., ultraviolet), ions, photons, electrons and other excited-state (e.g., metastable) species which are suitable for performing material property changes with high spatial, material selectivity, and temporal control. Plasmas may also remove a distinct upper layer of a workpiece with little or no effect on a separate underlayer of the workpiece or it may be used to selectively remove a particular tissue from a mixed tissue region or selectively remove a tissue with minimal effect to adjacent organs of different tissue type.

The plasma species are capable of modifying the chemical nature of tissue surfaces by breaking chemical bonds, substituting or replacing surface-terminating species (e.g., surface functionalization) through volatilization, gasification or dissolution of surface materials (e.g., etching). With proper techniques, material choices and conditions, one can remove one type of tissue entirely without affecting a nearby different type of tissue. Controlling plasma conditions and parameters (including S-parameters, V, I, $\Theta$, and the like) allows for the selection of a set of specific particles, which, in turn, allows for selection of chemical pathways for material removal or modification as well as selectivity of removal of desired tissue type.

The present disclosure provides a plasma catheter including a tubular member; a conductive cylindrical member; a first electrode; and a second electrode. The tubular member defines a longitudinal lumen therethrough and has a proximal portion and a distal portion. The conductive cylindrical member is disposed at the distal portion of the tubular member. The first electrode is embedded in a first side of the tubular member and coupled to the conductive cylindrical member. The second electrode is embedded in a second side of the tubular member diametrically opposed to the first side. The second electrode is offset from the tubular member and aligned with a center axis defined by the conductive cylindrical member.

According to one aspect of the present disclosure, the conductive cylindrical member is configured to concentrate an electrical field at the distal portion of the catheter such that an electrical field magnitude between the first electrode and the second electrode at the distal portion of the catheter is greater than an electrical field magnitude between the first electrode and the second electrode at a portion of the catheter proximal of the distal portion of the catheter.

According to another aspect of the present disclosure, the second electrode is embedded in a bulge of the second side of the tubular member.

According to another aspect of the present disclosure, the plasma catheter further includes a ceramic tubular member, and the conductive cylindrical member is disposed about the ceramic tubular member.

According to another aspect of the present disclosure, the ceramic tubular member includes mica, aluminum oxide, sapphire, zirconia, and/or polytetrafluoroethylene.

According to another aspect of the present disclosure, the first electrode includes copper and the second electrode includes tungsten.

According to another aspect of the present disclosure, the first electrode and the conductive cylindrical member include an insulating layer.

According to another aspect of the present disclosure, the first electrode and the second electrode are arranged in a double helix structure within at least a portion of the tubular member.

According to another aspect of the present disclosure, the double helix structure is configured to produce an inductance that mitigates a parasitic capacitance between the first electrode and the second electrode.

The present disclosure also provides a plasma system including a plasma catheter; an ionizable media source; and a generator. The plasma catheter includes a tubular member; a conductive cylindrical member; a first electrode; and a second electrode. The tubular member defines a longitudinal lumen therethrough and has a proximal portion and a distal portion. The conductive cylindrical member is disposed at the distal portion of the tubular member. The first electrode is embedded in a first side of the tubular member and coupled to the conductive cylindrical member. The second electrode is embedded in a second side of the tubular member diametrically opposed to the first side. The second electrode is offset from the tubular member and aligned with a center axis defined by the conductive cylindrical member. The ionizable media source is configured to provide ionizable media to the plasma catheter. The generator is configured to provide power to the plasma catheter to ignite the ionizable media to generate plasma.

According to another aspect of the present disclosure, an amount of the power provided to a distal portion of the plasma catheter produces a clinical bipolar tissue effect on a workpiece, and the effect includes biological decontamination, hemostasis, tissue necrosis, tissue vaporization, and/or ablation.

According to another aspect of the present disclosure, the ionizable media includes argon, helium, neon, krypton, xenon, radon, carbon dioxide, nitrogen, hydrogen, and/or oxygen, in gaseous form.

According to another aspect of the present disclosure, the plasma system further includes a precursor source configured to provide precursor feedstocks to the plasma catheter.

According to another aspect of the present disclosure, at least a portion of the plasma catheter is arranged within a flexible endoscope.

The present disclosure also provides a method of manufacturing a plasma catheter. The method includes embedding a first electrode in a first side of a tubular member that defines a longitudinal lumen therethrough and has a proximal portion and a distal portion. The first electrode is coupled to a conductive cylindrical member disposed at the distal portion of the tubular member. A second electrode is embedded in a second side of the tubular member diametrically opposed to the first side. The second electrode is offset from the tubular member and aligned with a center axis defined by the conductive cylindrical member.

According to another aspect of the present disclosure, the method of manufacturing a plasma catheter further includes inserting a ceramic tubular member into the distal portion of the tubular member, and positioning the conductive cylindrical member around the ceramic tubular member.

BRIEF DESCRIPTION OF THE DRAWINGS

The accompanying drawings, which are incorporated in and constitute a part of this specification, illustrate exemplary embodiments of the disclosure and, together with a general description of the disclosure given above, and the detailed description of the embodiments given below, serve to explain the principles of the disclosure, wherein.

DETAILED DESCRIPTION

Plasmas may be generated using electrical energy that is delivered as either direct current (DC) electricity or alternating current (AC) electricity at frequencies from about 0.1 hertz (Hz) to about 100 gigahertz (GHz), including radio frequency ("RF" from about 0.1 MHz to about 100 MHz) and microwave ("MW" from about 0.1 GHz to about 100 GHz) bands, using appropriate generators, electrodes, and antennas. Choice of excitation frequency, the workpiece, as well as the electrical circuits that are used to deliver electrical energy to the workpiece affect many properties and requirements of the plasma. The performance of the plasma chemical generation, the delivery system and the design of the electrical excitation circuitry are interrelated—as the choices of operating voltage, frequency and current levels, phase, and other electrical properties affect the electron temperature and electron density. Further, choices of electrical excitation and plasma device hardware also determine how a given plasma system responds dynamically to the introduction of new ingredients to the host plasma gas or liquid media. For instance, isolation and/or reduction of capacitance between two wires of a plasma device may be improved by employing a material having a relatively low dielectric constant, such as polyfluorenylene ethynylene (PFE) or polytetrafluoroethylene (PTFE, for example, TEFLON), as a dialectric material forming a tubular member of the plasma device.

Plasma beams may be used to coagulate, cauterize, or otherwise treat tissue through direct application of a high-energy plasma. In particular, kinetic energy transfer from the plasma to the tissue causes healing, and thus, affects thermal coagulation of bleeding tissue. Plasma beam coagulation utilizes a handheld electrosurgical instrument having one or more electrodes energizable by an electrosurgical generator, which outputs a high-intensity electric field suitable for forming plasma using ionizable media (e.g., inert gas).

In some cases, electrical energy is delivered to a workpiece by way of a bipolar plasma catheter that is sized to fit within a working channel of a flexible endoscope and may be employed, for example, in gastrointestinal procedures. As used herein, the term "bipolar" refers to a plasma system that includes a handheld electrosurgical instrument having both an active and a return electrode. The system does not include a separate return electrode coupled to the patient, thus isolating the patient from the electrosurgical generator. Electrosurgical energy is provided by a generator and forms an electric field between the electrodes contained within the instrument. In this configuration, plasma is generated within the instrument and is delivered to the patient as gas is pushed out of the instrument.

The two electrodes or wires are disposed along a central lumen of the bipolar plasma catheter. In some cases, the central lumen may have a relatively small inner or outer diameter from about 2 millimeters (mm) to about 4 mm. Electrical RF energy passing through the electrodes disposed in such proximity may give rise to significant capacitive coupling between the two electrodes. Such parasitic coupling results in a loss of electrosurgical energy along the length of the catheter, which in turn, produces insufficient power at the distal tip of the catheter and minor ionization of ionizable gas flowing down the lumen. Such minor ionization, while perhaps useful for pre-ignition of monopolar plasma energy, may be insufficient to create direct tissue effects by bipolar plasma.

The present disclosure provides for a plasma catheter and a plasma catheter system that overcome the drawbacks commonly associated with placing multiple electrodes within a small diameter lumen of the catheter. The plasma catheter according to the present disclosure includes two electrodes embedded in diametrically opposed sides of a tubular member (e.g., in respective bulges in the tubular member), thereby minimizing capacitive coupling between the two electrodes. At a distal portion of the catheter, a first one of the electrodes is electrically coupled to a conductive cylindrical member, and a second one of the electrodes is offset from the tubular member and aligned with a center of the conductive cylindrical member, thereby maximizing the delivery of electrical energy between the two electrodes at the distal portion of the catheter.

As used herein, the term "diametrically opposed" refers to two electrodes being positioned opposite (or approximately opposite) one other on opposite ends of a diameter of a circle as defined by a tubular member. In a case where a tubular member forms an oval shape, the two electrodes may be diametrically opposed by being positioned opposite (or approximately opposite) one other on opposite ends of the major axis of the oval formed by the tubular member, thereby maximizing the distance between the two electrodes and minimizing the capacitive coupling therebetween.

Figure 1:
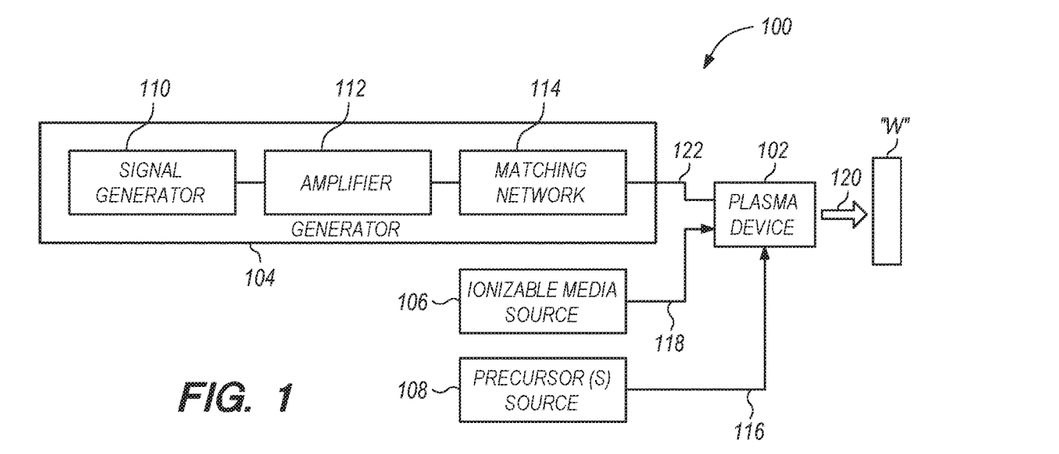
FIG. 1 is a schematic diagram of a plasma system according to the present disclosure.

Referring initially to FIG. 1, a plasma system 100 is disclosed. The system 100 includes a plasma device 102 that is coupled to a generator 104 (e.g., an electrosurgical generator), an ionizable media source 106 and a precursor(s) source 108. Generator 104 includes any suitable components for delivering power or matching impedance to plasma device 102. More particularly, the generator 104 may be any radio frequency generator or other suitable power source capable of producing power to ignite the ionizable media to generate plasma. The various example catheters described herein enable an amount of the power to be provided to the distal portion of the plasma catheter that produces a clinical bipolar tissue effect on a workpiece, such as, for example, biological decontamination, hemostasis, tissue necrosis, tissue vaporization, and/or ablation. The plasma device 102 may be utilized as an electrosurgical pencil for application of plasma to tissue and the generator 104 may be an electrosurgical generator that is adapted to supply the device 102 with electrical power at a frequency from about 0.1 MHz to about 2,450 MHz and in another embodiment from about 1 MHz to about 13.56 MHz. The plasma may also be ignited by using continuous or pulsed direct current (DC) electrical energy.

The precursor source(s) 108 may be a bubbler or a nebulizer configured to aerosolize precursor feedstocks prior to introduction thereof into the device 102. The precursor(s) source 108 may also be a microdroplet or injector system capable of generating predetermined refined droplet volume of the precursor feedstock from about 1 femtoliter to about 1 nanoliter in volume. The precursor(s) source 108 may also include a microfluidic device, a piezoelectric pump, or an ultrasonic vaporizer.

The system 100 provides a flow of plasma through the device 102 to a workpiece "W" (e.g., tissue). Plasma feedstocks, which include ionizable media and precursor feedstocks, are supplied by the ionizable media source 106 and the precursor(s) source 108, respectively, to the plasma device 102. During operation, the precursor feedstock and the ionizable media are provided to the plasma device 102 where the plasma feedstocks are ignited to form plasma effluent containing ions, radicals, photons from the specific excited species and metastables that carry internal energy to drive desired chemical reactions in the workpiece "W" (e.g., tissue) or at the surface thereof. The feedstocks may be mixed upstream from the ignition point or midstream thereof (e.g., at the ignition point) of the plasma effluent, as shown in FIG. 1 and described in more detail below.

The ionizable media source 106 provides ionizable feedstock, also referred to herein as ionizable media, to the plasma device 102. Suitable ionizable media include argon, helium, neon, krypton, xenon, radon, carbon dioxide, nitrogen, hydrogen, and/or oxygen, and combinations thereof in liquid and/or gaseous form. The ionizable media source 106 is coupled to the plasma device 102 and may include a storage tank and a pump (not explicitly shown). These and other gases may be initially in a liquid form that is gasified during application.

The precursor(s) source 108 provides precursor feedstock to the plasma device 102. The precursor feedstock may be either in solid, gaseous or liquid form and may be mixed with the ionizable media in any state, such as solid, liquid (e.g., particulates or droplets), gas, and the combination thereof. The precursor(s) source 108 may include a heater, such that if the precursor feedstock is liquid, it may be heated into gaseous state prior to mixing with the ionizable media.

In one embodiment, the precursors may be any chemical species capable of forming reactive species such as ions, electrons, excited-state (e.g., metastable) species, molecular fragments (e.g., radicals) and the like, when ignited by electrical energy from the generator 104 or when undergoing collisions with particles (electrons, photons, or other energy-bearing species of limited and selective chemical reactivity) formed from ionizable media 106. More specifically, the precursors may include various reactive functional groups, such as acyl halide, alcohol, aldehyde, alkane, alkene, amide, amine, butyl, carboxlic, cyanate, isocyanate, ester, ether, ethyl, halide, haloalkane, hydroxyl, ketone, methyl, nitrate, nitro, nitrile, nitrite, nitroso, peroxide, hydroperoxide, oxygen, hydrogen, nitrogen, and combination thereof. In embodiments, the chemical precursors may be water, halogenoalkanes, such as dichloromethane, tricholoromethane, carbon tetrachloride, difluoromethane, trifluoromethane, carbon tetrafluoride, and the like; peroxides, such as hydrogen peroxide, acetone peroxide, benzoyl peroxide, and the like; alcohols, such as methanol, ethanol, isopropanol, ethylene glycol, propylene glycol, alkalines such as NaOH, KOH, amines, alkyls, alkenes, and the like. Such chemical precursors may be applied in substantially pure, mixed, or soluble form.

The precursors and their functional groups may be delivered to a surface to react with the surface species (e.g., molecules) of the workpiece "W." In other words, the functional groups may be used to modify or replace existing surface terminations of the workpiece "W." The functional groups react readily with the surface species due to their high reactivity and the reactivity imparted thereto by the plasma. In addition, the functional groups are also reacted within the plasma volume prior to delivering the plasma volume to the workpiece.

Some functional groups generated in the plasma can be reacted in situ to synthesize materials that subsequently form a deposition upon the surface. This deposition may be used for stimulating healing, killing bacteria, and increasing hydrophilic or hydroscopic properties. In addition, deposition of certain function groups may also allow for encapsulation of the surface to achieve predetermined gas/liquid diffusion, e.g., allowing gas permeation but preventing liquid exchange, to bond or stimulate bonding of surfaces, or as a physically protective layer.

Figure 2:
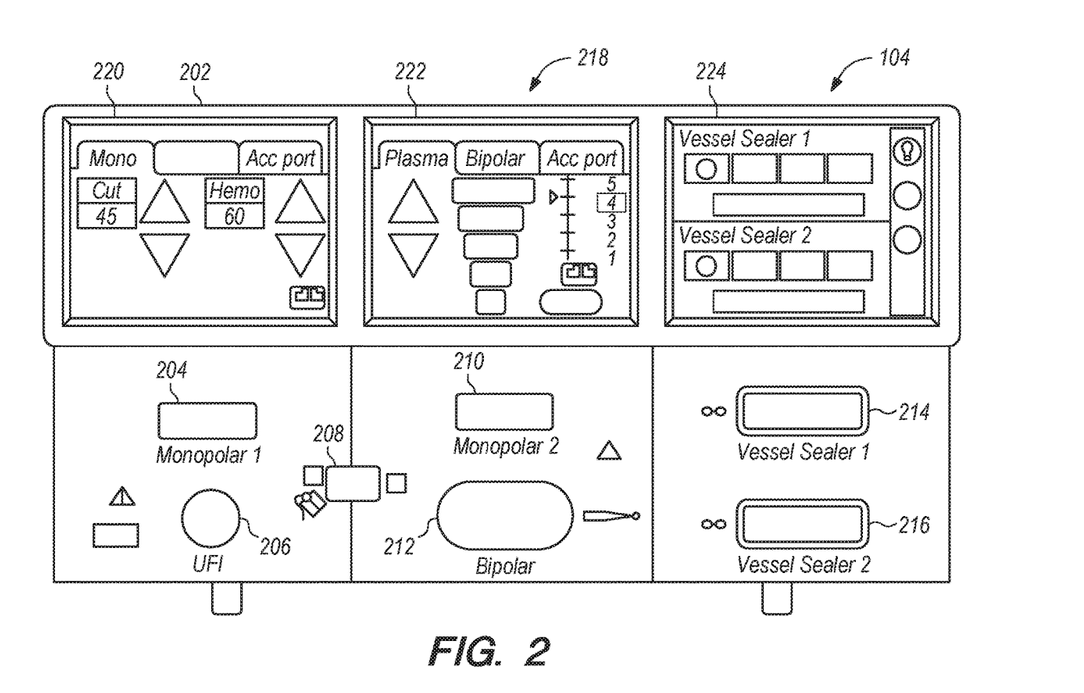
FIG. 2 is a front view of an embodiment of an electrosurgical generator according to the present disclosure.

With reference to FIG. 2, a front face 202 of the generator 104 is shown. The generator 104 may be any suitable type (e.g., electrosurgical, microwave, etc.) and may include a plurality of connectors 204, 206, 208, 210, 212, 214, and 216 to accommodate various types of electrosurgical instruments (e.g., electrosurgical forceps, electrosurgical pencils, ablation probes, etc.) in addition to a plasma instrument (e.g., plasma instrument 102, not shown in FIG. 2).

The generator 104 includes a user interface 218 having one or more display screens 220, 222, 224 for providing the user with variety of output information (e.g., intensity settings, treatment complete indicators, etc.). Each of the screens 220, 222, 224 is associated with a corresponding subset of the connectors 204, 206, 208, 210, 212, 214, and 216, as shown in FIG. 2 and as described in further detail below. The generator 104 includes suitable input controls (e.g., buttons, activators, switches, touch screen, etc.) for controlling the generator 104. The display screens 220, 222, 224 are also configured as touch screens that display a corresponding menu for the electrosurgical instruments (e.g., a plasma instrument, etc.). The user then adjusts inputs by simply touching corresponding menu options.

Screen 220 controls monopolar output and the devices connected to the connectors 204 and 206. Connector 204 is configured to couple to a monopolar electrosurgical instrument (e.g., electrosurgical pencil) and connector 206 is configured to couple to a foot switch (not shown in FIG. 2). The foot switch provides for additional inputs (e.g., replicating inputs of the generator 104). Screen 222 controls monopolar, plasma and bipolar output and the devices connected to the connectors 210 and 212. Connector 210 is configured to couple to other monopolar instruments. Connector 212 is configured to couple to a plasma instrument (e.g., plasma instrument 102, not shown in FIG. 2).

Connector 208 may be used to connect to one or more return electrode pads (not shown in FIG. 2). The return electrode pad may be coupled to the generator 104 via a return pad cable, which is coupled to the connector 208 via a plug (not shown in FIG. 2). The return electrode pad may be coupled to a polarization controller (not shown), which in turn is coupled to the connector 208. Screen 224 controls plasma procedures performed by a plasma instrument (e.g., plasma instrument 102) that may be plugged into the connectors 214 and 216.

Figure 3:
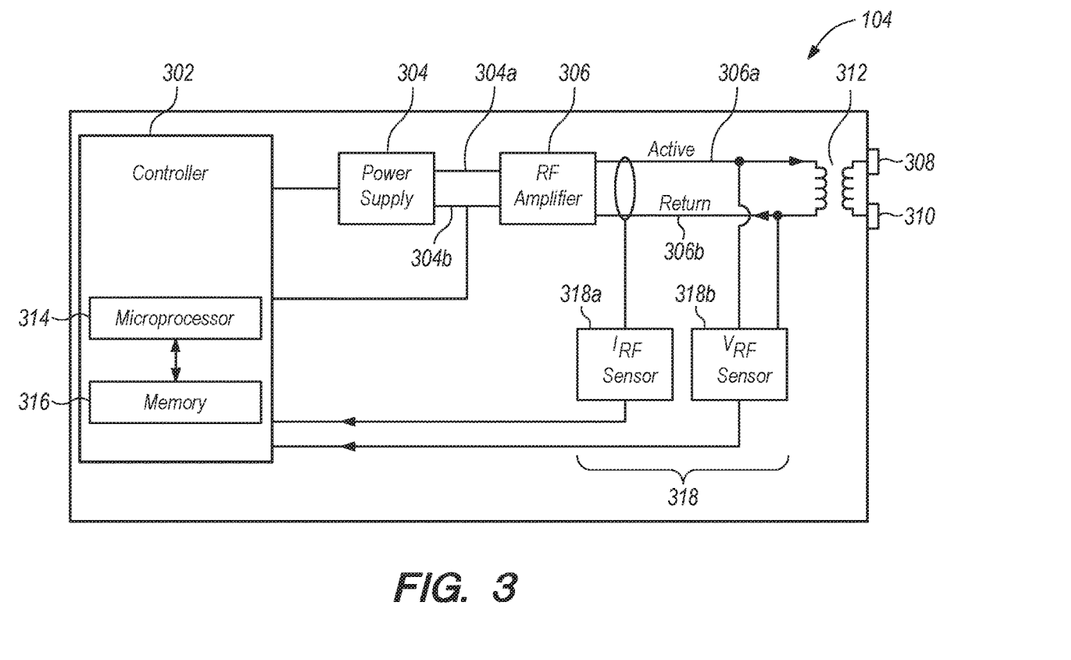
FIG. 3 is a schematic block diagram of an embodiment of the electrosurgical generator of FIG. 2 according to the present disclosure.

FIG. 3 shows a schematic block diagram of the generator 104 configured to output electrosurgical energy. The generator 104 includes a controller 302, a power supply 304, and a radio-frequency (RF) amplifier 306. The power supply 304 may be a high voltage, DC power supply connected to an AC source (e.g., line voltage) and provides high voltage, DC power to the RF amplifier 306 via leads 304a and 304b, which then converts high voltage, DC power into treatment energy (e.g., electrosurgical or microwave) and delivers the energy to the active terminal 308. The energy is returned thereto via the return terminal 310. The active and return terminals 308 and 310 are coupled to the RF amplifier 306 through an isolation transformer 312. The RF amplifier 306 is configured to operate in a plurality of modes, during which the generator 104 outputs corresponding waveforms having specific duty cycles, peak voltages, crest factors, etc. It is envisioned that in other embodiments, the generator 104 may be based on other types of suitable power supply topologies.

The controller 302 includes a processor 314 operably connected to a memory 316, which may include transitory type memory (e.g., RAM) and/or non-transitory type memory (e.g., flash media, disk media, etc.). The processor 314 includes an output port that is operably connected to the power supply 304 and/or RF amplifier 306 allowing the processor 314 to control the output of the generator 104 according to either open and/or closed control loop schemes. A closed loop control scheme is a feedback control loop, in which a plurality of sensors measure a variety of tissue and energy properties (e.g., tissue impedance, tissue temperature, output power, current and/or voltage, etc.), and provide feedback to the controller 302. The controller 302 then signals the power supply 304 and/or RF amplifier 306, which adjusts the DC and/or power supply, respectively. Those skilled in the art will appreciate that the processor 314 may be substituted by using any logic processor (e.g., control circuit) adapted to perform the calculations and/or set of instructions described herein including, but not limited to, field programmable gate array, digital signal processor, and combinations thereof.

The generator 104 according to the present disclosure includes a plurality of sensors 318, e.g., an RF current sensor 318a, and an RF voltage sensor 318b. Various components of the generator 104, namely, the RF amplifier 306, the RF current and voltage sensors 318a and 318b, may be disposed on a printed circuit board (PCB). The RF current sensor 318a is coupled to the active terminal 308 and provides measurements of the RF current supplied by the RF amplifier 306. In embodiments the RF current sensor 318a may be coupled to the return terminal 310. The RF voltage sensor 318b is coupled to the active and return terminals 308 and 310 provides measurements of the RF voltage supplied by the RF amplifier 306. In embodiments, the RF current and voltage sensors 318a and 318b may be coupled to active and return leads 306a and 306b, which interconnect the active and return terminals 308 and 310 to the RF amplifier 306, respectively.

The RF current and voltage sensors 318a and 318b provide the sensed RF voltage and current signals, respectively, to the controller 302, which then may adjust output of the power supply 304 and/or the RF amplifier 306 in response to the sensed RF voltage and current signals. The controller 302 also receives input signals from the input controls of the generator 104 and/or the plasma instrument 102. The controller 302 utilizes the input signals to adjust the power output of the generator 104 and/or performs other control functions thereon.

Figure 4:
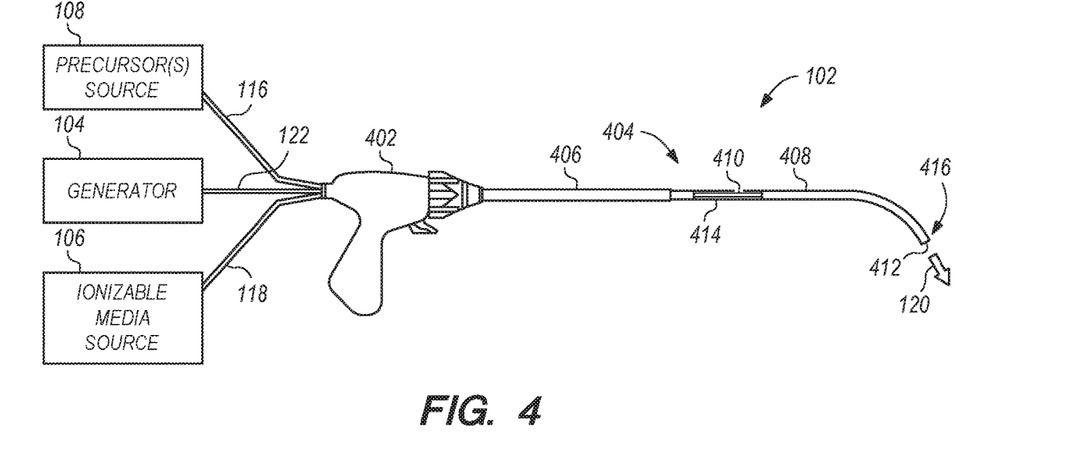
FIG. 4 is a schematic view of a plasma device according to the present disclosure.

FIG. 4 is a schematic view of the plasma device 102 according to the present disclosure. With reference to FIGS. 1 and 4, the precursor(s) source 108 and the ionizable media source 106 may be coupled to the plasma device 102 via tubing 116 and 118, respectively. The tubing 116 and 118 may be combined into unified tubing to deliver a mixture of the ionizable media and the precursor feedstock to the device 102 at a proximal end thereof. This allows for the plasma feedstocks, e.g., the precursor feedstock and the ionizable gas, to be delivered to the plasma device 102 simultaneously prior to ignition of the mixture therein.

In another embodiment, the ionizable media source 106 and the precursor(s) source 108 may be coupled to the plasma device 102 via the tubing 116 and 118 at separate connections, such that the mixing of the feedstocks occurs within the plasma device 102 upstream from the ignition point. In other words, the plasma feedstocks are mixed proximally of the ignition point, which may be any point between the respective sources 106 and 108 and the plasma device 102, prior to ignition of the plasma feedstocks to create the desired mix of the plasma effluent species for each specific surface treatment on the workpiece "W."

In a further embodiment, the plasma feedstocks may be mixed midstream, e.g., at the ignition point or downstream of the plasma effluent, directly into the plasma. It is also envisioned that the ionizable media may be supplied to the device 102 proximally of the ignition point, while the precursor feedstocks are mixed therewith at the ignition point. In a further illustrative embodiment, the ionizable media may be ignited in an unmixed state and the precursors may be mixed directly into the ignited plasma. Prior to mixing, the plasma feedstocks may be ignited individually. The plasma feedstock is supplied at a predetermined pressure to create a flow of the medium through the device 102, which aids in the reaction of the plasma feedstocks and produces a plasma effluent. The plasma according to the present disclosure is generated at or near atmospheric pressure under normal atmospheric conditions.

With continued reference to FIG. 4, the device 102 includes a handle 402 and a catheter 404 having a proximal portion 406 that is coupled to the handle 402 and a distal portion 408. The catheter 404 includes a tubular member 414 defining a lumen 410 therein and extending the entire length thereof and terminating in an opening 412 at the distal portion 416 of the distal portion 408. The catheter 404 may have a diameter from about 2 mm to about 10 mm, in embodiments, from about 3 mm to about 5 mm (for example, for compatibility with a working channel of an endoscope having a diameter of 1.6 mm, 2.4 mm, or 3.8 mm), allowing the device 102 to be inserted through operating ports for application of the plasma effluent 120 at the operating site during endoscopic or endoluminal procedures or through natural body orifices.

In one exemplary embodiment, the distal portion 408 is configured for controlled deflection. A pull-wire (not shown in FIG. 4) or another suitable actuation mechanism extends from the handle 402 at the proximal end of the device 102 through a lumen in the catheter 404 and is fastened to the distal portion 408. The pull-wire is movable from a first generally relaxed position wherein the distal portion 408 is disposed in a generally longitudinally-aligned position relative to the proximal portion 406 to a second retracted or tensed position wherein the distal portion 408 flexes (e.g., deflects) from the proximal portion 406 at a desired angle as shown in FIG. 4.

The distal portion 408 is constructed to be more flexible than the proximal portion 406, such that when the handle 402 is pulled back or otherwise actuated, the pull-wire bends the distal portion 408 from an undeflected position to a deflected position. The pull-wire may be attached to the outside of a ceramic tubular member 510 (FIG. 7A), or the pull-wire may be an additional polymer fiber attached to the lumen structure 410 and free from the lumen 410 at a proximal end of the flexed portion of the catheter 404. In particular, the proximal portion 406 may include a wire or other support materials (not shown) therein to provide tensile strength to the catheter 404 while still maintaining flexibility for maneuvering through a vascular system. The distal portion 408 is formed from a flexible biocompatible material such as polytetrafluoroethylene, polyurethane, polyimide, polyether block amide (PEBAX), and the like to allow for maneuverability thereof.

The device 102 includes two or more electrodes 504 and 506 (e.g., a return electrode and an active or working electrode, respectively), which are described in further detail below, with respect to FIGS. 5A-10. In embodiments, the electrodes 504 and 506 may be formed as wire electrodes (e.g., pointed tip), and may be disposed within the tubular member 414 so as to minimize capacitive coupling between the electrodes 504 and 506 at the proximal portion 406 while maximizing the electric field between the external and internal conductors at the distal portion 416 of the catheter 404 to ignite ionizable media and form plasma.

The electrodes 504 and 506 are disposed through the catheter 404 and are connected to the generator 104 via electrical cable 122. The ionizable media source 106 and the precursor(s) source 108 may include various flow sensors and controllers (e.g., valves, mass flow controllers, etc.) to control the flow of ionizable media to the device 102. In particular, the lumen 410 is in gaseous and/or liquid communication with the ionizable media source 106 and the precursor(s) source 108 allowing for the flow of ionizable media and precursor feedstocks to flow through the catheter 404 to the distal portion 408. The ionizable media in conjunction with the precursor feedstocks is ignited by application of energy through the electrodes 504 and 506 to form the plasma plume 120 exiting through the opening 412.

Figures 5A, 5B:
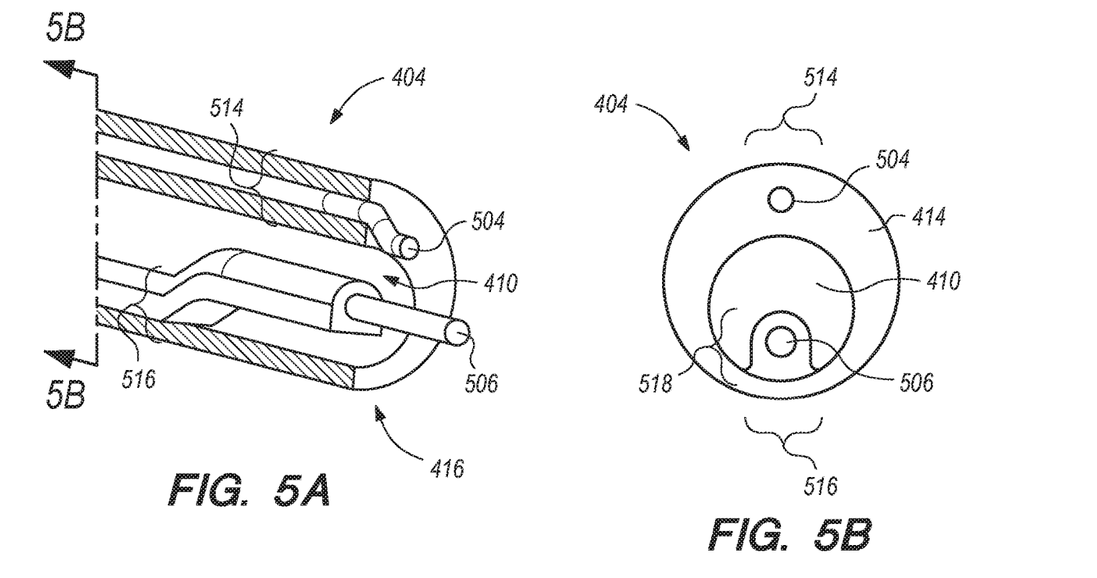
FIG. 5A is a perspective cross-sectional view of a distal portion of a partially-assembled plasma catheter of the plasma device of FIG. 4 according to an embodiment of the present disclosure.
FIG. 5B is a cross-sectional view taken along line 5B of the distal portion of the partially-assembled plasma catheter of FIG. 5A according to an embodiment of the present disclosure.

FIG. 5A is a perspective cross-sectional view of a distal portion 416 of the plasma catheter 404 in a partially-assembled form. The catheter 404 includes the tubular member 414 that defines the lumen 410 by which the ionizable media is delivered. The catheter 404 also includes a first electrode 504 and a second electrode 506. The first and second electrodes 504 and 506 may be formed from any suitable electrically conducting material. In example embodiments, the electrodes 504 and 506 may be formed from wires that have an inductance rating at about 473 kHz of approximately 7.37 pH and a capacitance at 1 MHz of 32.0 pF to yield a cable self resonance of about 10.4 MHz. A diameter of the first electrode 504 and/or a diameter of the second electrode 506 may be, for example, from about 0.001 inches to about 0.020 inches, in embodiments from about 0.005 inches to about 0.015 inches. In some exemplary embodiments herein, at least a portion of the first electrode 504 and/or the second electrode 506 may be covered by an insulating material.

As shown in FIG. 5A, the first electrode 504 is embedded in a first side 514 of the tubular member 414, and the second electrode 506 is embedded in a second side 516 of the tubular member 414, which is diametrically opposed to the first side 514. In embodiments, the second electrode 506 may be embedded in a bulge 518 extending either the lumen 410. In further embodiments, the bulge 518 may extend outwardly and be disposed outside the lumen 410. The first electrode 504 may be embedded in the first side 514 without being embedded in a bulge, other variations on this configuration are contemplated such as only one of the electrodes 504, 506 being disposed within the bulge 518 or alternatively, both electrodes 504, 506 being disposed within their respective bulges 518 or in further embodiments, both electrodes 504, 506 being directly disposed within the tubular member 414.

Figure 7A:
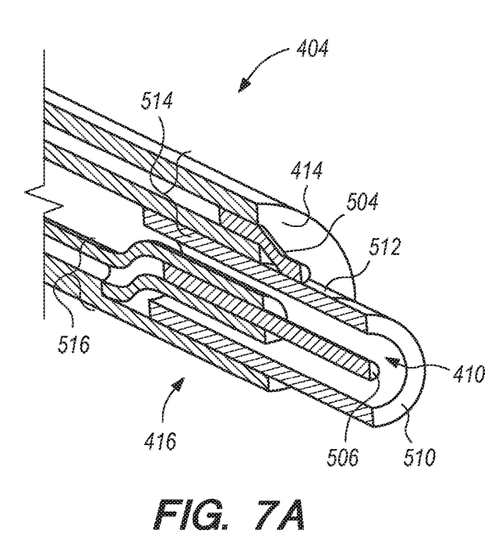
FIG. 7A is a perspective cross-sectional view of the distal portion of the plasma catheter of the plasma device of FIG. 4 according to an embodiment of the present disclosure.
Figure 7B:
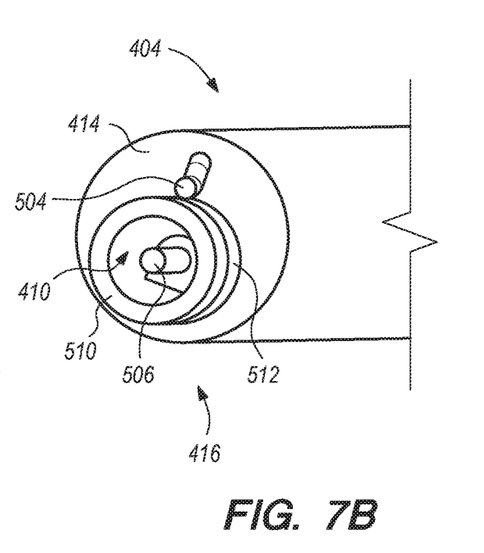
FIG. 7B is a perspective view of the distal portion of the plasma catheter of the plasma device of FIG. 4 according to an embodiment of the present disclosure.
Figure 8:
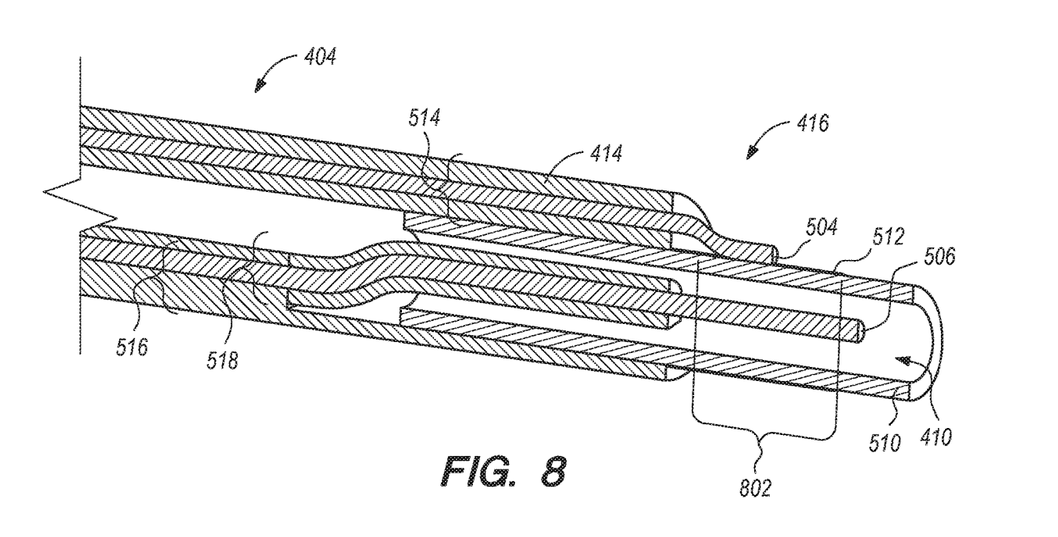
FIG. 8 shows an enlarged perspective cross-sectional view of the distal portion of the plasma catheter of the plasma device of FIG. 4 according to an embodiment of the present disclosure.
Figure 9:
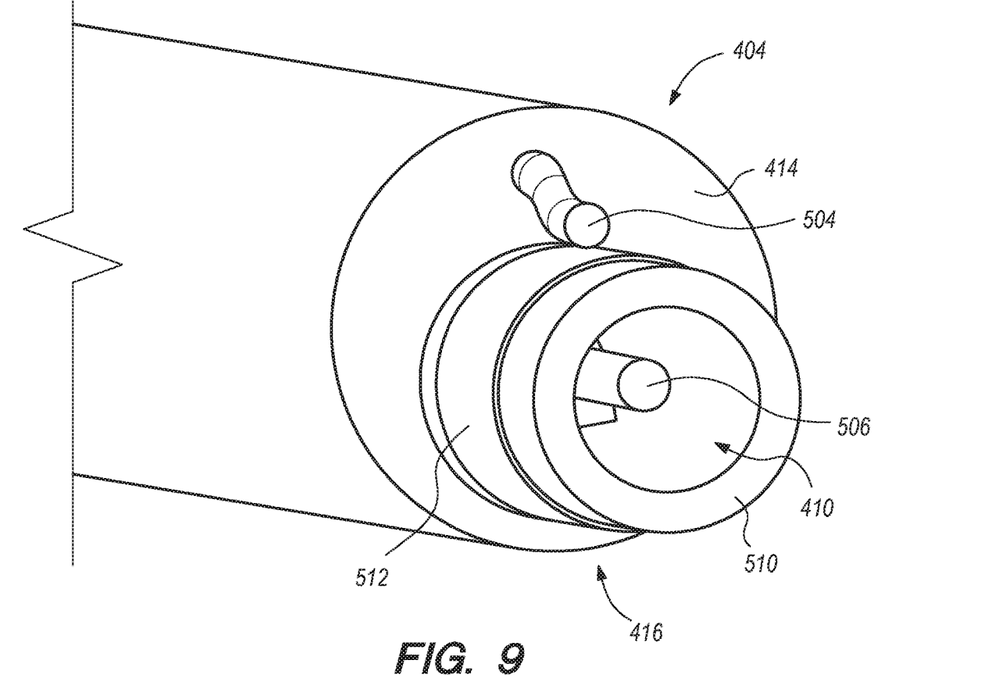
FIG. 9 shows an enlarged perspective view of the distal portion of the plasma catheter of the plasma device of FIG. 4 according to an embodiment of the present disclosure.

At the distal portion 416 of the catheter 404, the second electrode 506 is offset from the tubular member 414 and is arranged so as to be substantially aligned with a center of the lumen 410, which may substantially align with a center of a conductive cylindrical member 512 as described below with respect to FIGS. 7A and 7B. The second electrode 506 may be offset by skiving a portion of the tubular member 414, namely the bulge 518, and then bending a distal portion of the second electrode 506 to align in the desired configuration.

Arrangement of the first electrode 504 and the second electrode 506 in diametrically opposed sides 514, 516 of the tubular member 414 throughout the proximal portion 406 of the catheter 404 maximizes a distance between the first electrode 504 and the second electrode 506. This configuration of the electrodes 504 and 506 minimizes capacitive coupling between the first electrode 504 and the second electrode 506. As described in further detail below in connection with FIGS. 7A and 7B, at a distal portion of the catheter 404, the first electrode 504 and the second electrode 506 are offset from their respective sides of the tubular member 414 and are arranged so as to maximize the delivery of electrical energy between the first and second electrodes 504 and 506 at the distal portion 416 of the catheter 404.

FIG. 5B shows a cross-sectional view taken along line 5B of the distal portion of the plasma catheter 404 in a partially-assembled form. As apparent from FIG. 5B, the first electrode 504 is embedded in the first side 514 of the tubular member 414 and the second electrode 506 is embedded in a bulge 518 of the second side 516 of the tubular member 414, the bulge 518 and the second side 516 being diametrically opposed to the first side 514. The lumen 410 is disposed through the catheter 404.

The plasma catheter 404 can be manufactured using single or multiple extrusions. In a single extrusion procedure, the electrodes 504 and 506 are extruded within a sheath material (e.g., a polymer) in a single extrusion, thereby disposing the electrodes 504 and 506 within the tubular member 414 that is formed from the sheath material and defines the lumen 410 therein. Alternatively, in a double extrusion, the electrodes 504 and 506 are extruded in two separate extrusion steps. Initially, the electrode 506 can be extruded within a first sheath material (e.g., polytetrafluoroethylene) in a first extrusion step, thereby disposing the electrode 506 within a bulge 518 formed from the first sheath material. Then, the electrode 506, once disposed within the bulge 518, is fed together with the electrode 504 into an extruder to be extruded within a second sheath material (e.g., polyfluorenylene ethynylene (PFE) or another suitable polymer) in a second extrusion step, thereby disposing the electrodes 504 and 506 within the tubular member 414 that is formed from the second sheath material and defines the lumen 410 therein.

Figure 6:
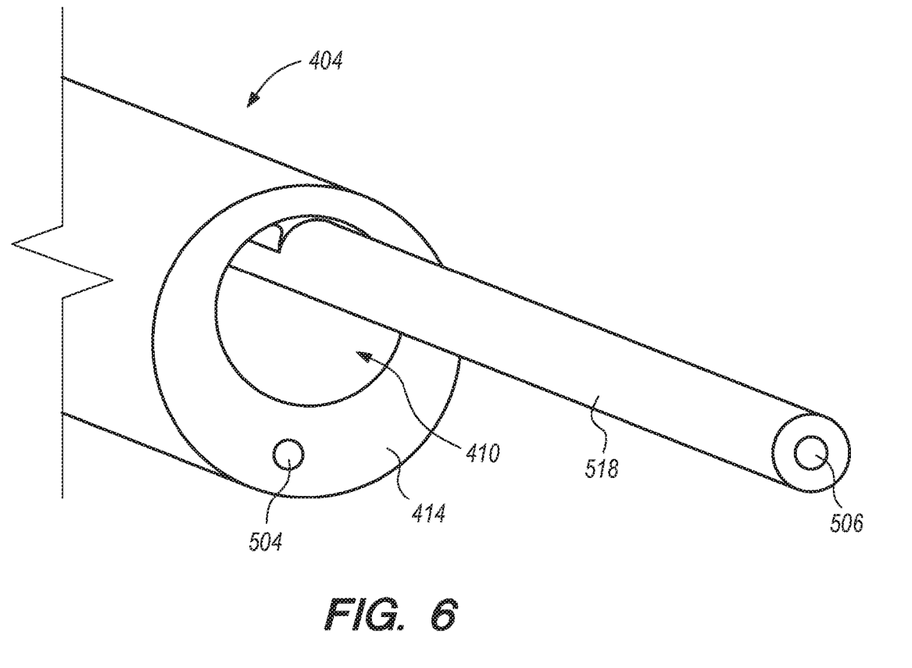
FIG. 6 shows a perspective cross-sectional view of the catheter 404 formed by double extrusion, according to an embodiment of the present disclosure.

FIG. 6 shows a perspective cross-sectional view of the catheter 404 formed by a double extrusion procedure. As shown in FIG. 6, the catheter 404 includes the electrode 504 disposed within the tubular member 414 and the electrode 506 disposed within the bulge 518. For illustrative purposes, in FIG. 6 the electrode 506 and the bulge 518, which are formed in the first extrusion step, are shown as extending beyond the electrode 504 and tubular member 414.

Reference will now be made to FIGS. 7A, 7B, 8, and 9, which show the distal portion of the plasma catheter 404. The plasma catheter 404 includes a ceramic tubular member 510, which is inserted into the distal portion 416 of the catheter 404 and a metallic ring 512 is positioned around and/or secured to an outside of the ceramic tubular member 510. The ceramic tubular member 510 may be formed from any suitable insulating materials capable of withstanding high-temperatures, such as, for instance, mica, aluminum oxide, sapphire, zirconia, polytetrafluoroethylene (for example, TEFLON), and combinations thereof, selected for high temperature, high dielectric strength, and relatively high dielectric constant, for example.

At the distal portion 416 of the catheter 404, the first electrode 504 is electrically coupled to the metallic ring 512. The second electrode 506 is offset from the tubular member 414 and is substantially aligned with a center of the metallic ring 512, which encircles the second electrode 506. In embodiments, the first electrode 504 may be formed from a first metal including, but not limited to, copper and may be electrically soldered or welded to the metallic ring 512 at the distal portion 416 of the catheter 404, and the second electrode 506 may be formed from a second metal sufficient to handle relatively high energy levels (e.g., an energy level sufficient to produce a clinical bipolar tissue effect), such as by way of example and not limitation, tungsten or tungsten alloy with thorium.

The metallic ring 512 is configured to concentrate an electrical field at a distal portion 416 of the catheter 404 (e.g., at distal portion 802, where the metallic ring 512 encircles the second electrode 506), such that an electrical field magnitude between the first electrode 504 and the second electrode 506 at the distal portion 416 of the catheter 404 is greater than an electrical field magnitude between the first electrode 504 and the second electrode 506 at the proximal portion 406 of the catheter 404 allowing for ionization of the ionizable media.

In embodiments, the catheter 404 may include multiple metallic rings 512 and/or scalloped metallic rings. In this case, at the distal portion 416 of the catheter, the first electrode 504 is electrically coupled to each of the metallic rings 512, and the second electrode 506 is offset from the tubular member 414 and aligned with the respective centers of each of the metallic rings 512.

The metallic ring 512 may be formed as a layer (e.g., as a metal trace, printed conducting ink, and/or foil) so as to concentrate the electric field on the outside of the ceramic tubular member 510, to maximize the electrical communication between the first electrode 504 and the second electrode 506 at the distal portion 416 of the catheter 404. In embodiments, the metallic ring 512 may be formed such that its width in a direction perpendicular to a central axis of the lumen 410 is less than its width in a direction parallel to a central axis of the lumen 410. In further embodiments herein, the metallic ring 512 may be covered by an insulating material and/or the metallic ring 512 may have a saw-toothed edge.

The first electrode 504 and the second electrode 506 of the catheter 404 may also be arranged in a double helix structure in at least a proximal portion 406 of the catheter 404, thereby producing an inductance that mitigates a parasitic capacitance created by the parallel electrodes 504, 506 used in the catheter 404. In some embodiments, a parasitic capacitance between the first electrode 504 and the second electrode 506 may be less than 4 picoFarads per foot of length.

Figure 10:
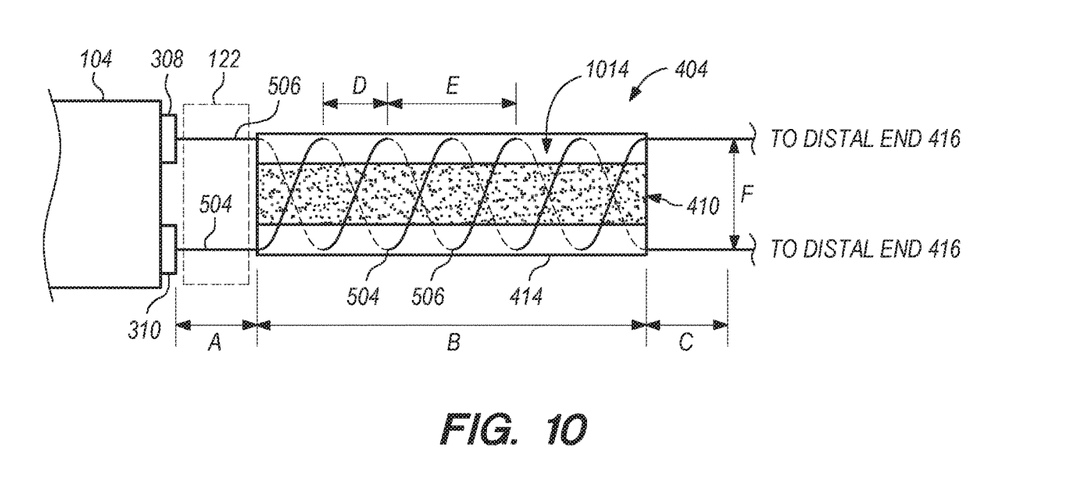
FIG. 10 is a cross-sectional view of a proximal portion of the plasma catheter of the plasma device of FIG. 4 according to an embodiment of the present disclosure.

With reference to FIG. 10, which shows a cross-sectional view of the catheter 404, the electrodes 504 and 506 are operatively connected to the generator 104 via connectors 308 and 310, respectively. The electrodes 504 and 506 extend from the connectors 308 and 310, respectively, for a distance A, which can be optimally controlled by the location of connectors 308 and 310, and may be from approximately 0.1 inches to approximately 6 inches. The electrodes 504 and 506 are then helix wound in a wound portion 1014, which may be from approximately 7 feet or more, depending upon a desired cable inductance and capacitance. Alternatively, the wound portion 1014 may extend from the connectors 308 and 310 without extending the electrodes 504 and 506 for the distance A.

The wound portion 1014, along catheter length B, can be of any length depending on geometric configuration and physical properties (e.g., tensile strength, flexibility, etc.) of materials used in manufacturing of catheter components. More specifically the electrodes 504 and 506 are oriented in a double helix which includes two congruent helixes with the same axis, differing by a translation along the axis. The electrodes 504 and 506 may be oriented in a plurality of other arrangements which wrap the electrodes 504 and 506 around themselves. The arrangement of the electrodes 504 and 506 in a double helix orients the opposing electrical fields generated by the electrosurgical RF energy passing therethrough to mitigate and/or cancel out thereby minimizing the amount of lost stray electrical RF energy.

With continued reference to FIG. 10 and the portion 1014, the distance D, which represents the distance between one apex of one helix and a nearest apex of another helix, may be, for example, approximately ½ inch. The distance E, which is the distance between two apexes of the same helix may be, for example, approximately 1 inch. The outer diameter F of the catheter 404 may, for example, be about ⅜ of an inch.

The catheter 404, as illustrated in FIG. 10, provides a transmission medium to deliver RF energy from the generator 104 to a tissue site. The catheter 404 represents one example of a preferred embodiment for the RF transmission medium, which reduces the radiated RF electrical field and maximizes the applied clinical treatment energy delivered to the tissue site. The dimensions A, B, C, D, E and F of FIG. 10 form a unique proximal geometric relationship in three dimensional space to control the electrical field coupling between the active and return output terminals of the generator 104 to significantly reduce the electrical field radiation by field cancellation.

The physical dimensions A, B, C, D, E and F are interdependent and optimized to provide a low loss inductive and capacitive transmission medium, which in addition to controlling the electrical field, reduces uncontrolled capacitive coupling caused by stray RF radiation. In particular, the following equations (1) and (2) illustrate the interdependent relationship of dimensions A, B, C, D, E and F with respect to inductive and capacitive properties of the catheter 404.

$$\text{Inductance} = B(10.16 \times 10^{-9}) \text{Ln}[(2 \times D)/d] + 2(A+C) \quad (\mu\text{H/in. for specified wire}) \quad (1)$$

$$\text{Capacitance} = [(B \times (0.7065 \times 10^{-12}))/\text{Ln}[(2 \times D)/d]] er \quad (2)$$

In equations (1) and (2), d denotes diameter of the wire (e.g., electrodes 504, 506), er denotes the dielectric constant of the wire insulator. Further, E=2×D, the ratio of E to D allows to establish a continuum of the helix configuration and F=k×D, where k is a constant from about 0.5 to about 1.5.

Although not shown in FIG. 10, at the distal portion 416 of the catheter 404, the electrodes 504 and 506 may be unwound and disposed in the manner described above in connection with FIGS. 5A, 5B, 6, 7A, 7B, 8, and 9, so as to maximize the delivery of electrical energy between the two electrodes at the distal portion 416 of the catheter 404. The electrodes 504 and 506 extend a distance C from the portion 1014 to the distal portion 408 in an unwound state. The initial length A of the electrodes and the unwound state length C are maintained relatively consistent with varying lengths of wire with length of the wound portion 1014 varying for different overall lengths.

The catheter 404 according to the present disclosure orients the electrodes 504 and 506 so that the electrical fields generated therethrough are mitigated and/or substantially canceled (except at the distal portion 416), thereby reducing the amount of leaked stray RF energy. More specifically, placement and orientation of the electrodes 504 and 506 in the manner discussed above provides for close proximity of electrical fields generated during transmission of electrosurgical RF energy and maximizes amount of energy delivered to the treatment site. Reducing the electrical fields also increases safety of personnel and the patient.

Reduced RF radiation decreases capacitive and RF field leakage and improves RF control of the delivered energy. Reduced RF radiation also decreases RF transmission loss and improves efficiency of the generator 104 by reducing RF harmonic component, minimizing corruption of the RF source and reducing peripheral conductive and radiative emissions. Further, reducing RF radiation also decreases the RF noise to additional equipment found in the room, such as patient monitoring equipment.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A method for using a plasma system comprising:
   supplying ionizable media from an ionizable media source to a plasma catheter; and
   supplying electrical power from a generator to the plasma catheter to ignite the ionizable media to generate plasma,
   wherein the plasma catheter includes:
      a tubular member defining a longitudinal lumen therethrough and having a proximal portion and a distal portion;
      a conductive cylindrical member disposed at the distal portion of the tubular member;
      a first electrode embedded in a first side of the tubular member and coupled to the conductive cylindrical member arranged to provide an electrical return path; and
      a second electrode embedded, at the proximal portion, in a second side of the tubular member diametrically opposed to the first side, the second electrode being offset from the tubular member at the distal portion and aligned with a center axis defined by the conductive cylindrical member.

2. The method of claim 1, wherein the conductive cylindrical member is configured to concentrate an electrical field at the distal portion of the catheter such that a first magnitude of the electrical field between the first electrode and the second electrode at the distal portion of the catheter is greater than a second magnitude of the electrical field between the first electrode and the second electrode at a portion of the catheter proximal of the distal portion of the catheter.

3. The method of claim 1, wherein the second electrode is embedded in a bulge of the second side of the tubular member.

4. The method of claim 1, wherein the plasma catheter further includes a ceramic tubular member and the conductive cylindrical member is disposed about the ceramic tubular member.

5. The method of claim 4, wherein the ceramic tubular member includes at least one of mica, aluminum oxide, sapphire, zirconia, or polytetrafluoroethylene.

6. The method of claim 1, wherein the first electrode includes copper and the second electrode includes tungsten.

7. The method of claim 1, wherein the first electrode and the conductive cylindrical member include an insulating layer.

8. The method of claim 1, wherein the first electrode and the second electrode are arranged in a double helix structure within at least a portion of the tubular member.

9. The method of claim 8, wherein the double helix structure is configured to produce an inductance that mitigates a parasitic capacitance between the first electrode and the second electrode.

10. The method of claim 1, wherein an amount of the power provided to a distal portion of the plasma catheter produces a clinical bipolar tissue effect on a workpiece, the effect including at least one of biological decontamination, hemostasis, tissue necrosis, tissue vaporization, or ablation.

11. The method of claim 1, wherein the ionizable media is a gas and includes at least one of argon, helium, neon, krypton, xenon, radon, carbon dioxide, nitrogen, hydrogen, or oxygen.

12. The method of claim 1, the method further including supplying precursor feedstocks, from a precursor source to the plasma catheter.

13. The method of claim 1, wherein at least a portion of the plasma catheter is arranged within a flexible endoscope.

* * * * *